US010286120B2

(12) United States Patent
Tomantschger et al.

(10) Patent No.: US 10,286,120 B2
(45) Date of Patent: *May 14, 2019

(54) IN-VIVO BIODEGRADABLE MEDICAL IMPLANT COMPRISING A MICROSTRUCTURE ENGINEERED METALLIC MATERIAL

(71) Applicant: INTEGRAN TECHNOLOGIES, INC., Mississauga (CA)

(72) Inventors: Klaus Tomantschger, Mississauga (CA); Gino Palumbo, Toronto (CA); Diana Facchini, Toronto (CA)

(73) Assignee: INTEGRAN TECHNOLOGIES, INC., Mississauga (CA)

( * ) Notice: Subject to any disclaimer, the term of this patent is extended or adjusted under 35 U.S.C. 154(b) by 392 days.

This patent is subject to a terminal disclaimer.

(21) Appl. No.: 14/826,611

(22) Filed: Aug. 14, 2015

(65) Prior Publication Data

US 2016/0038653 A1     Feb. 11, 2016

Related U.S. Application Data

(63) Continuation of application No. 12/232,764, filed on Sep. 24, 2008, now Pat. No. 9,119,906.

(51) Int. Cl.
*A61L 31/14*      (2006.01)
*A61L 17/10*      (2006.01)
(Continued)

(52) U.S. Cl.
CPC ............. *A61L 31/148* (2013.01); *A61L 17/10* (2013.01); *A61L 31/022* (2013.01); *A61L 31/06* (2013.01);
(Continued)

(58) Field of Classification Search
CPC .... A61L 31/148; A61L 31/022; A61L 27/446; A61L 27/54; A61L 27/56; A61L 27/58;
(Continued)

(56) References Cited

U.S. PATENT DOCUMENTS 3,687,135 A    8/1972   Stroganov et al.
5,352,266 A    10/1994  Erb
(Continued)

FOREIGN PATENT DOCUMENTS

CA    2441578 A1    9/2002
CA    2584896 A1    4/2006
(Continued)

OTHER PUBLICATIONS

"Microstructural Development in Friction Welded AZ31 Magnesium Alloy", Fukumoto et al., Materials Transactions, vol. 47, No. 4, Apr. 15, 2006.
(Continued)

*Primary Examiner* — Seema Mathew
(74) *Attorney, Agent, or Firm* — Bacon & Thomas, PLLC

(57) ABSTRACT

In-vivo biodegradable medical implants, containing at least in part at least partially fine-grained metallic materials provide a strong, tough, stiff and lightweight implant. The in-vivo biodegradable implants are used in a number of stent applications, for fracture fixation, sutures and the like. The in-vivo biodegradable medical implants enable the reduction of implant size and weight and consequently result in reducing the release of implant degradation products into the body.

22 Claims, 2 Drawing Sheets

(51) Int. Cl.
| | |
|---|---|
| *A61L 31/12* | (2006.01) |
| *A61L 31/18* | (2006.01) |
| *A61L 31/02* | (2006.01) |
| *A61L 31/06* | (2006.01) |
| *A61L 31/16* | (2006.01) |

(52) U.S. Cl.
CPC ........... *A61L 31/124* (2013.01); *A61L 31/128* (2013.01); *A61L 31/16* (2013.01); *A61L 31/18* (2013.01); *A61F 2310/00011* (2013.01)

(58) Field of Classification Search
CPC ...... A61L 31/128; A61L 31/146; A61L 31/16; A61L 27/042; A61L 27/04; A61L 7/10; A61L 31/14; A61F 2002/30062; A61F 2002/30677; A61F 2002/30957; A61F 2002/30968; A61F 2002/3098; A61F 2002/30981; A61F 2310/00011; A61F 2310/00017; A61F 2310/00083
See application file for complete search history.

(56) References Cited

U.S. PATENT DOCUMENTS

| | | | |
|---|---|---|---|
| 5,400,633 A | 3/1995 | Sagal | |
| 5,433,797 A | 7/1995 | Erb et al. | |
| 5,837,030 A | 11/1998 | Schulz et al. | |
| 5,980,564 A | 11/1999 | Stinson | |
| 6,019,784 A | 2/2000 | Hines | |
| 6,174,330 B1 | 1/2001 | Stinson | |
| 6,287,332 B1 | 9/2001 | Bolz | |
| 6,333,093 B1 | 12/2001 | Burrell et al. | |
| 6,991,647 B2 | 1/2006 | Jodhav | |
| 7,096,705 B2 | 8/2006 | Sagal | |
| 8,025,979 B2 | 9/2011 | Palumbo et al. | |
| 2002/0004060 A1 | 1/2002 | Heublein | |
| 2004/0045402 A1 | 3/2004 | Boily et al. | |
| 2004/0098108 A1 | 5/2004 | Harder | |
| 2005/0131522 A1 | 6/2005 | Stinson et al. | |
| 2005/0205425 A1 | 9/2005 | Palumbo | |
| 2005/0209680 A1 | 9/2005 | Gale et al. | |
| 2006/0020289 A1 | 1/2006 | Kuttler | |
| 2006/0079953 A1 | 4/2006 | Gregorich et al. | |
| 2006/0122687 A1* | 6/2006 | Bassler | A61F 2/82 623/1.15 |
| 2006/0135282 A1* | 6/2006 | Palumbo | A01K 87/00 473/316 |
| 2006/0259126 A1 | 11/2006 | Lenz | |
| 2006/0292388 A1 | 12/2006 | Palumbo | |
| 2007/0050009 A1 | 3/2007 | Flanagan | |
| 2007/0135908 A1* | 6/2007 | Zhao | A61L 31/022 623/1.46 |
| 2007/0191708 A1 | 8/2007 | Gerold et al. | |
| 2007/0265354 A1 | 11/2007 | Canham | |
| 2007/0281176 A1 | 12/2007 | Palumbo et al. | |
| 2008/0031765 A1* | 2/2008 | Gerold | C22C 23/00 420/404 |
| 2008/0103594 A1* | 5/2008 | Loffler | A61L 27/047 623/11.11 |
| 2008/0140199 A1 | 6/2008 | Briest | |
| 2008/0160259 A1 | 7/2008 | Nielson et al. | |
| 2008/0175885 A1* | 7/2008 | Asgari | A61L 27/446 424/426 |
| 2008/0177378 A1 | 7/2008 | Asgari | |
| 2008/0188922 A1 | 8/2008 | Stinson | |
| 2008/0213611 A1 | 9/2008 | Asgari | |
| 2008/0249608 A1 | 10/2008 | Dave | |
| 2008/0249638 A1* | 10/2008 | Asgari | A61F 2/28 623/23.75 |
| 2009/0081313 A1 | 3/2009 | Aghion et al. | |
| 2009/0192595 A1 | 7/2009 | Nagura et al. | |
| 2009/0198320 A1* | 8/2009 | Mueller | A61L 31/022 623/1.38 |
| 2010/0076544 A1 | 3/2010 | Hoffman et al. | |
| 2010/0087915 A1* | 4/2010 | Bayer | A61L 31/022 623/1.46 |
| 2010/0131050 A1* | 5/2010 | Zhao | A61L 31/022 623/1.42 |
| 2010/0137971 A1 | 6/2010 | Lootz et al. | |
| 2010/0185299 A1 | 6/2010 | Nies | |
| 2010/0211164 A1* | 8/2010 | McClain | A61F 2/82 623/1.46 |
| 2010/0262221 A1* | 10/2010 | Schafer | A61F 2/07 623/1.13 |
| 2010/0272778 A1* | 10/2010 | McClain | A61F 2/82 424/423 |
| 2011/0313538 A1 | 12/2011 | Oh et al. | |
| 2014/0097277 A1* | 4/2014 | Kumta | A61L 31/148 241/15 |
| 2014/0107740 A1 | 4/2014 | Crisp | |
| 2014/0120324 A1 | 5/2014 | Cully | |
| 2014/0364960 A1 | 12/2014 | Meyer-Kobbe et al. | |
| 2015/0080998 A1 | 3/2015 | Mueller et al. | |
| 2016/0263287 A1* | 9/2016 | Zhang | A61L 31/06 |
| 2017/0312102 A1* | 11/2017 | Mangiardi | A61K 31/436 |

FOREIGN PATENT DOCUMENTS

| | | | | |
|---|---|---|---|---|
| EP | 1803475 | A2 | 7/2007 | |
| EP | 1959025 | A1 | 8/2008 | |
| WO | 03035130 | A1 | 5/2003 | |
| WO | WO 2007125532 | A2 * | 11/2007 | ........... A61L 27/047 |
| WO | 2008092435 | A2 | 8/2008 | |
| WO | 2008/122595 | A2 | 10/2008 | |

OTHER PUBLICATIONS

"Effect of Grain Size on Mechanical Property of Mg—3Al—1Zn Alloy", Wang et al., Scripta Materialia, vol. 59, Mar. 4, 2008.
European Office Action for EP 09709438.7, dated May 3, 2013.
R.Z. Valiev and T.G. Langdon, "Principles of Equal Channel Angular Pressing a Processing Tool for Grain Refinement", Progress in Materials Science 51 (2006) 881-981; Elsevier Ltd, New York, USA.
KH. Saber, C.C. Koch and P.S. Fedkiv, "Pulse Electrodeposition of Nanocrystalline Zinc", Materials Science and Engineering A341 (2003) 174-181; Elsevier Ltd, New York, USA.

* cited by examiner

IN-VIVO BIODEGRADABLE MEDICAL IMPLANT COMPRISING A MICROSTRUCTURE ENGINEERED METALLIC MATERIAL

FIELD OF THE INVENTION

This invention is directed to the use of at least partially fine-grained metallic articles or their components for biodegradable medical devices, specifically implants. Isotropic, multilayered, and/or graded layers optimized for "local" performance requirements are employed for producing or coating stents, sutures, fracture fixation devices and other medical devices having an in-vivo degradation time of over one month.

BACKGROUND OF THE INVENTION

A number of operative procedures require the use of metal screws, nails, plates, fasteners, rods, pins, wire structures, suture anchors and staples to aid in the reconstruction of bone fractures, torn ligaments and other injuries as well as for closing wounds. Balloon-expandable coronary stents find use in the treatment of coronary artery disease by providing an alternative to balloon angioplasty and bypass surgery. Stents are thin walled tubular-shaped devices which counteract significant decreases in vessel or duct diameter by supporting the conduit by a mechanical scaffold. In addition to stenting coronary arteries, stenting is widely used in other natural body conduits, such as central and peripheral arteries and veins, bile ducts, esophagus, colon, trachea or large bronchi, ureters, and urethra.

Long-term implants can have damaging effects on the body and, where applicable, some may need to be eventually removed, thus requiring surgery. Certain implants including stents cannot be removed at all. Permanent metal implants can increase the risk of infection due to the presence of a foreign material in the body.

To alleviate undesired side effects of implants, medical device manufacturers have developed biodegradable materials that can be absorbed by the body over time. These biodegradable implants, also referred to as in-vivo degradable, absorbable, resorbable, bioresorbable and bioabsorbable, are made of various materials that will diminish in mass over time within the body. Essentially, once biodegradable material implants such as stents, sutures, staples, plates or screws have aided in healing the injury or the medical condition and are no longer required, they slowly degrade/dissolve in the body, eliminating the need for removal surgery.

"Permanent implants" are typically made of stainless steel, cobalt alloys or nickel-titanium alloys. Fracture fixation devices are relatively thick (200 microns to 5 mm) and are placed using conventional open surgery. Other implants such as stents are implanted in the "radially collapsed state" by a catheter which is inserted at an easily accessible location and then advanced through the vasculature to the deployment site. Once in position, the stent is deployed by inflation of a dilation balloon. Stents have a relatively thin wall thickness (50 to 200 microns) and, as remote insertion is used for their placements, stents need to be visualized with X-ray based fluoroscopy procedures.

"Permanent stents" which remain in place indefinitely cause problems if multiple stents or restenting is required as they are impossible to remove and can cause in-stent restenosis. According to the American Heart Association the two main benefits of intracoronary stents are (i) the treatment of dissections and (ii) the prevention of restenosis; these benefits are realized during the first few months after implantation. Coronary dissections are effectively contained by stent insertion and undergo a healing process, with the majority of cardiac events occurring in the first six months. Stent prevention restenosis also occurs within the first six months. Therefore, a stent that is in place beyond six months has no clear function and "temporary stents" such as biodegradable stents offer the same near term benefits as "permanent stents" without the potential risk for long-term complications. Furthermore, the use of biodegradable stents enables multiple stenting and restenting.

"Biodegradable stents" have been proposed to address a short-term need for a stent. A first approach was to use biodegradable polymers and the first biodegradable stents were implanted in animals in 1988. A polymer of poly-L-lactide was used which could withstand up to 1,000 mm Hg of crush pressure and kept its radial strength for one month. The stent was almost completely degraded after nine months. Biodegradable stents made of polyglycolic acid were evaluated in canines in the early 1990s. Unfortunately, during the absorption process most polymers cause inflammation leading to severe intimal hyperplasia or thrombotic occlusions. This is overcome in the present invention by including a biodegradable metallic material as a principal stent constituent.

Stinson in U.S. Pat. No. 5,980,564 (1999) U.S. Pat. No. 6,174,330 (2001), Jodhav in U.S. Pat. No. 6,991,647 (2006) and Flanagan in US 2007/0050009 describe biodegradable polymeric stents.

While polymer based biodegradable stents have received most attention, metal based biodegradable stents have been developed as well. Magnesium alloy-based stents have been tested in animals and humans. The Lekton Magic coronary stent is laser cut from an absorbable magnesium alloy tube. Alloy composition is used to modulate the time required for complete biocorrosion and dissolution times range from one day to two months. As magnesium is one of the most important micronutrients, degradation products are not expected to have any side effects. Magnesium stents, however, are radiolucent causing difficulties with detection of stent embolization, confirmation of complete stent expansion and apposition with precise placement of overlapping stents. These disadvantages can be overcome in the present invention by using iron and/or zinc as a principal stent constituent for a stent.

Harder in US US20040098108A1 (2004) describes intraluminal endoprostheses such as stents, comprising a carrier structure which contains a magnesium alloy of the following composition by weight: magnesium: >90%, yttrium: 3.7%-5.5%, rare earths: 1.5%-4.4% and balance: <1%. The balloon-expandable carrier structure is cut by a laser from a precursor tube.

Heublein in US20020004060A1 (2002) discloses metallic medical implants. After fulfilling its temporary support function, the implant degrades by corrosion at a predetermined rate. Negative long-term effects are thus avoided. The use of metals provides superior mechanical properties. The corrosion rate of the implant is set by the appropriate choice of materials. The main constituent is selected from the group consisting of alkali metals, alkaline earth metals including magnesium, iron, zinc and aluminum. The biological, mechanical and chemical properties of the materials can be beneficially affected if a subsidiary constituent is provided in the form of manganese, cobalt, nickel, chromium, copper, cadmium, lead, tin, thorium, zirconium, silver, gold, palladium, platinum, rhenium, silicon, calcium, lithium, aluminum, zinc, iron, carbon or sulfur. The preferred material is either an alloy of magnesium with a content of up to 40% lithium plus addition of iron, or an iron alloy with a small amount of aluminum, magnesium, nickel and/or zinc. Suitable corrosion rates are achieved by an alloy or a sintered metal made of approximately equal parts of zinc and iron.

Bolz in U.S. Pat. No. 6,287,332 (2001) describes implantable bioresorbable vessel wall supports, especially coronary stents using a combination of metals which decompose in the human body without any harmful effects. The combination of metallic materials is designed such that the material of the vessel wall support dissolves at a certain decomposition rate and without the production of bio-incompatible decomposition products. For correspondingly uniform corrosion to be obtained, such an alloy comprises a component selected from one or several metals of the group consisting of magnesium, titanium, zirconium, niobium, tantalum, zinc and silicon which covers itself with a protective oxide coating. For uniform dissolution of the mentioned oxide coating to be attained, a second component is added to the alloy, possessing sufficient solubility in blood or interstitial fluid, such as lithium, sodium, potassium, calcium, iron or manganese. The combination of a passivating and a soluble component ensures a timely and uniform decomposition into biocompatible breakdown products. The corrosion rate can be regulated through the ratio of the two components.

Loffler in US 2008/0103594 (2008) describes absorbable medical implant composites comprising a matrix made of a crystalline magnesium containing bio-corrosive alloy. The implant is reinforced either with bio-corrosive alloy fibers selected from the group consisting of magnesium, calcium, iron and yttrium or non-biodegradable fiber materials. Suitable reinforcements include amorphous or nanocrystalline fibers made by melt-spinning, which, compared to crystalline materials, provide increased strength and delayed in-vivo corrosion.

Generally stents are formed by a two step process, namely (i) drawing of a suitable tube precursor followed by (ii) suitably perforating it into the desired stent pattern i.e. by laser cutting. Alternative fabrication methods include direct forming e.g. using electroforming or sputtering.

Hines in U.S. Pat. No. 6,019,784 (2000) describes a process for electroforming an expandable stent by (i) coating an electrically-conductive mandrel with a suitable resist material, (ii) exposing the resist to an appropriate light pattern and frequency so as to form a stent pattern in the resist, (iii) electroplating the mandrel with a suitable stent material and (iv) etching away the temporary mandrel once a sufficient layer of stent material is deposited, leaving a completed stent. According to Hines a suitable stent material is selected for biocompatibility and mechanical characteristics. It must be sufficiently ductile to be radially expandable to form an appropriate intra vascular endoprosthesis and sufficiently rigid to hold its shape once the expansion force is removed. It must also be sufficiently inert to be biocompatible and resistant to etching solutions. Gold and various gold alloys generally satisfy these requirements because they are generally inert and resistant to corrosion from bodily fluids and, also are resistant to a wide variety of etching solutions. Other metals which have specific beneficial characteristics as stent materials include silver, nickel, platinum, rhodium, palladium, iron and various alloys of these metals. It is anticipated that high gold, platinum, or nickel alloys with from about 95 to about 100 percent content of such metals would produce stents with highly desirable characteristics. Selection of particular materials for the stent is based primarily upon biocompatibility and mechanical characteristics.

The use of biodegradable metallic implants for the reconstruction of bone fractures and or closing wounds has a long history as demonstrated below.

Stroganov in U.S. Pat. No. 3,687,135 (1972) describes magnesium alloys for use in fracture fixation. Magnesium-based alloys are disclosed which provide high mechanical strength, do not result in vigorous gas-evolution and have a rate of absorption which is slower than the process of bone consolidation.

Kuttler in US20060020289 describes biocompatible and bioabsorbable suture and clip material for surgical purposes comprising biodegradable magnesium alloys which can remain in the wound as the suture and clip material is absorbed by the body and which, by virtue of their compositions, improve protection from wound infections and promote the healing process.

The employment of grain-refinement to specifically enhance mechanical properties of metallic materials has been described as demonstrated below.

Erb in U.S. Pat. No. 5,352,266 (1994), and U.S. Pat. No. 5,433,797 (1995) describes a process for producing nanocrystalline metals, particularly nanocrystalline nickel. Nanocrystalline materials are electrodeposited onto the cathode in an aqueous acidic electrolytic cell by application of a pulsed current to produce wear resistant coatings, magnetic materials and catalysts for hydrogen evolution.

Palumbo in US Patent Application Publication No. US 2005-0205425 A1 discloses a process for forming coatings or free-standing deposits of nanocrystalline metals, metal alloys or metal matrix composites at high deposition rates. The process employs tank, drum plating or selective plating processes.

Tomantschger in U.S. Ser. No. 12/003,224 filed Dec. 20, 2007 describes means for electroplating metallic materials with varying properties in a single plating cell including fine-grained, coarse grained and amorphous metals and alloys.

Segal in U.S. Pat. No. 5,400,633 (1993) discloses a method for deformation processing of metals by extrusion through a die assembly with two channels having equal cross sectional areas under near frictionless conditions and in U.S. Pat. No. 7,096,705 (2006) Segal describes a shear-extrusion method of severe plastic deformation for the fabrication of metal shapes with ultra-fine microstructures. These method have been identified as being suitable for achieving grain-refinement in metals and alloys.

SUMMARY OF THE INVENTION

This invention relates to biodegradable implants at least partially containing fine-grained metallic materials. A biodegradable medical implant comprises, for example:

(a) from 5 to 100% by weight or volume of a metallic material and (b) from 95 to 0% by weight or volume of a polymeric material;

where from 5 to 100% of the metallic material has a crystalline microstructure with an average grain size ranging from 2 nm to 10 µm;

said implant having a thickness ranging from 5 µm to 2.5 cm;

the metallic material, average grain size and thickness being such that the implant degrades entirely in-vivo in a time ranging from one month to twelve months; and/or (a) from 5 to 99% by weight biodegradable polymer or magnesium;

(b) from 1 to 95% by weight of a metallic material comprising iron and/or zinc with 5 to 100% by weight of the iron and/or zinc having a crystalline microstructure with an average grain size ranging from 2 nm to 10 µm and having a hardness ranging from 25 to 3,000 VHN, said metallic material comprising iron and/or zinc being present in the form of a coating layer and/or in the form of metallic fillers selected from the group consisting of ribbons, powders, chips, fibers and flakes, said implant having a thickness ranging from 5 µm to 2.5 cm;

said thickness being such that the implant degrades entirely in-vivo in a time ranging from one month to twelve months.

Preferred metallic materials include iron or iron alloys which are radiopaque although other metals and alloys including zinc-based and/or magnesium-based materials can be used. Pure iron includes "electrolytic pure iron", defined as containing ≥98% by weight iron, preferably ≥99.5% by weight iron. Preferred iron alloys contain >75% by weight iron, preferably >90% by weight iron and more preferably >95% by weight iron and up to 98% by weight iron. Particularly preferred metallic materials comprise >98% by weight pure metals selected from the group consisting of iron, magnesium and zinc with unavoidable impurities or alloys containing at least 55% by weight of one or more metals selected from the group consisting of iron, magnesium and zinc.

Biodegradable metallic materials are applied as coatings, fillers or in free-standing form and completely biodegrade in bodily fluids. Articles made from at least partially fine-grained metallic materials comprising electrolytic pure iron or iron-alloys are particularly suitable for use in biodegradable implants. Due to their enhanced strength at least partially fine-grained metallic materials enable the reduction of the total volume and weight of implants. According to this invention, suitable biodegradable metallic materials and their in-vivo corrosion products do not result in local or systemic toxicity.

As used herein "at least partially fine-grained" defines a microstructure having an average grain size in the range between 2 nm and 10 microns and includes structures where the grain size is uniform (isotropic microstructure) or non-uniform (anisotropic microstructure) in which case the microstructure varies, e.g., through the cross-section, e.g. by grading and/or layering. Varying the grain size of the metallic deposit can be used to affect a number of properties including the hardness, yield strength, ultimate tensile strength, toughness, Young's modulus, resilience, elastic limit, ductility, internal and residual stress, stiffness, coefficient of friction, electrical conductivity and corrosion resistance including the corrosion rate in bodily fluids. If the microstructure is graded and/or multilayered, at least one section of the metallic material having a thickness of at least 1.5 nm contains isotropic microstructure fine-grained metallic material. Graded and multilayered microstructures, however, can also include amorphous and/or coarse-grained (grain size >10 micron) sections.

Overall the at least partially fine-grained microstructure metallic material (average crystalline microstructure group size ranging from 2 nm to 10 µm) is contained in a single layer or multiple layers representing in total at least 5% and up to 100% of the weight/volume and/or the cross-section layer thickness of the metallic structure and/or the biodegradable implant article with any remainder of the metallic structure and/or implant article being coarse-grained or amorphous biodegradable metallic materials. A graded or multilayered material is preferably synthesized by an electrodeposition process by suitably adjusting the electrodeposition conditions in a single tank to produce functionally graded and multilayered structures as disclosed in U.S. patent application Ser. No. 12/003,224. Other suitable synthesis processes for preparing at least partially fine-grained microstructure metallic material include physical or chemical vapor deposition, cold spraying and severe plastic deformation (SPD) including equal channel annular pressing (ECAP), accumulative roll bonding (ARB) and compressive torsion processing (CTP). One or more properties of the deposit can be either progressively graded or multilayered or more or less abruptly modified during the deposition process to provide layered deposits with selected properties changing stepwise from layer to layer. As used herein the term "graded and multilayered" refers to a property, e.g., the grain size, being altered by at least 10% and, for example, by as much as 2,500 fold by either effecting a gradual or abrupt property change in the direction of the deposit. One or more properties such as grain size and chemical composition can be caused to differ at one outer surface compared to another outer surface by suitably modifying the process conditions. The differences in value of the grain size and/or other properties in the deposition direction do not necessarily have to be differences in values between the inner and the outer surface of the deposit, as long as the minimum property value throughout the cross section of the deposit varies from the maximum value of the same property by at least 10%. Combinations of gradual and abrupt property changes are possible as well and can be readily achieved using electrodeposition.

Electrodeposition, physical vapor deposition (PVD), chemical vapor deposition (CVD), and cold spraying are linear deposition processes and therefore properties within the deposit layer of a deposit usually remain constant while selected properties in the direction of the deposit change as the deposition conditions are varied. In the case of electrodeposition the direction of the deposit is defined as the direction of the current flow between anode and cathode in the plating cell and the resulting build-up in the electrodeposited layer on the cathode, i.e., if the cathode is a flat plate the direction of the deposit is perpendicular to the cathode. If the cathode substrate is a rod or a tube, which is rotated against the anode during metal deposition, the direction of the deposit is in the radial direction. Linear deposition processes can, however, also be adjusted to change the properties of the deposit in the plane/layer thereby grading the structure in one or more directions.

As used herein "coarse-grained" defines a metallic microstructure having an average grain size greater than 10 micron and up to 500 micron. "At least partially fine-grained" is defined as a metallic microstructure having an average grain size between 2 nm and 10 micron. As used herein "amorphous" defines a metallic microstructure lacking crystallinity characterized by a pattern of constituent atoms or molecules which do not repeat periodically in the three dimensions.

The prior art on biodegradable metallic implants exclusively relies on alloying to achieve the desired biological, chemical and mechanical properties of the implant. Alloying usually requires the introduction of at least small amounts of undesired and potentially toxic elements as, e.g., practiced in current biodegradable magnesium-based implants. In contrast, this invention relates to a suitable refinement and optimization of the microstructure as the preferred approach to vary mechanical properties including the yield strength, toughness and stiffness as well as chemical properties including the bio-corrosion rate. Grain refinement (i.e., Hall-Petch strengthening) substantially enhances mechanical strength thereby reducing the mass/volume of the article. Specifically to biodegradable implants, grain-refinement is therefore considered superior to using alloying as grain-refinement provides lightweight articles with high specific-strength without the introduction of undesired/toxic elements. The bio-corrosion rate is adjusted to the desired level preferably by grain-refinement and/or by chemical composition adjustments (alloying, metal matrix composites, employment of biodegradable polymers). Composite designs of at least partially fine-grained metallic materials and biodegradable polymers are another preferred option including coating biodegradable polymer articles or their precursors with at least partially fine-grained metals/alloys on at least part of the inner or outer surface and/or reinforcing biodegradable polymer articles or their precursors with fibers, ribbons, spines, flakes and powders of at least partially fine-grained metals/alloys.

It is an objective of the invention to provide light-weight articles comprising at least partially fine-grained metallic materials, preferably comprising one or more metals selected from the group of iron, magnesium and zinc that have a high fracture toughness and fatigue resistance, are strong, sufficiently ductile, wear and abrasion resistant, as well as biodegradable in bodily fluids and which can be manufactured by a convenient and cost-effective process.

It is an objective of the invention to employ a manufacturing process for preparing, reinforcing or coating biodegradable implants comprising at least partially fine-grained metallic materials as well as preparing at least partially fine-grained metallic fillers (i.e. powders, chips, fibers, flakes, spines and ribbons) for use as reinforcement, e.g., in biodegradable polymers, which is simple, economic and capable of consistently producing uniform high quality devices or their components with superior mechanical and biological properties.

It is an objective of the invention to provide biodegradable medical implants wherein at least partially fine-grained metallic materials are applied and are present in at least one form selected from the group consisting of layers, coatings, plates, tapes, tubes, perforated tubes, complex shapes, particles, chips, spines, fibers and flakes.

It is an objective of the invention to employ a manufacturing process to prepare the biodegradable implant retaining at least partially fine-grained microstructure by avoiding processes involving exposing the at least partially fine-grained material to temperatures exceeding half of their melting temperature expressed in degrees in degrees Kelvin thus avoiding grain-growth.

It is an objective of the invention to prepare biodegradable implants with alternating metallic layers of similar or dissimilar chemical composition, e.g., comprising iron, with a microstructure selected from the group of amorphous, at least partially fine-grained and coarse-grained materials, by a convenient manufacturing process selected from electroplating, PVD, CVD, cold spraying and severe plastic deformation. Structures of dissimilar chemical composition include, e.g., alternating between iron and magnesium layers or between metallic coatings, e.g. zinc coated iron, iron coated magnesium and/or zinc coated magnesium, as can be readily synthesized in the form of plates, foils, wires, and more complex structures.

It is an objective of the invention to net-shape electroform biodegradable components to mimic the geometry of the implant at the deployment site. It is frequently preferred to shape the vessel wall support structures including stents on "molds" which mimic the geometry of the vessel or vessels to be stented. Similarly, in the case of fracture fixation, it is desired to shape plates to reasonably well match the shape, i.e., curvature and diameter of the bone at the fracture location and refrain from using flat plates which are not in intimate contact with the bone surface. This can be achieved by forming, e.g., a suitable wax mold by rapid prototyping, followed by metalizing the mold, forming the biodegradable article and removing it from the mold (e.g. by melting the mold).

It is an objective of the invention to provide biodegradable composite structures comprising a biodegradable polymer and at least in part at least partially fine-grained metallic material, wherein the metallic material is applied as coating to at least part of an external or internal biodegradable polymer substrate surface, as layers, e.g., in biodegradable polymer/metal laminates, or as backbone with the biodegradable polymeric material applied over part or all of the biodegradable metallic structure. Again, iron is a preferred metallic material due to iron and iron-based alloys being radiopaque and therefore conveniently imaged.

It is an objective of the invention to reinforce biodegradable polymers, at least in part, with at least partially fine-grained biodegradable metallic structures in the form of ribbons, fibers, flakes, spines and powders. The aspect ratio of such biodegradable metallic fillers preferably is 2:1 or greater and up to 1,000:1. Notwithstanding the particle size/actual size of the metallic particulate additions, said metallic reinforcement additions also have at least in part a crystalline microstructure with an average grain size between 2 nm and 10,000 nm to maintain superior physical properties such as hardness, yield strength, ultimate tensile strength and the like. Said metallic reinforcement additions can also have microstructures which are not isotropic including partially or totally fine-grained, coarse-grained and/or amorphous microstructures.

It is an objective of the invention to apply isotropic or quasi-isotropic metallic coatings or coating sub-layers by electrodeposition to minimize columnar, elongated grains and any texture in contrast to, e.g., conventional iron, steel or magnesium comprising tubes and sheets fabricated by conventional deep drawing, rolling or plating techniques.

It is an objective of the invention to provide biodegradable medical devices containing at least one at least partially fine-grained metallic layer comprising in preferably one or more metals selected from the group of iron, magnesium and zinc with improved biocompatibility and mechanical properties.

It is an objective of the invention to provide biodegradable articles serving as aids in the reconstruction of bone fractures, torn ligaments and other injuries including screws, nails, flat plates, curved plates, fasteners, rods, pins, wire structures, suture anchors clips and staples.

It is an objective of the invention to provide biodegradable vessel support structures comprising iron capable of accurate placement and expansion. It is an objective of the invention to provide biodegradable stents which are radiopaque or fluoroscopically visible under X-ray to allow accurate stent placement and stent expansion using real-time visualization to track the delivery catheter through the patient's vasculature and to enable the precisely placement of the stent at the site of a lesion.

It is an objective of the invention to render biodegradable vessel support structures which are radiopaque including at least a partial coating comprising iron and/or reinforcing zinc-based, magnesium-based or polymer-based implants with iron structures to achieve the desired imaging requirements. Alloying suitable metals with Fe to enhance the radiopaque properties is contemplated as well.

It is an objective of the invention to provide vessel support structures/stents which can be used to treat coronary diseases, esophageal disease (stenting proximal or mid-esophageal malignant strictures), gastroduodenal obstructions (stenting for palliation of malignant gastroduodenal and small intestinal obstructions), colorectal obstruction (stenting the colon and rectum area for long-term colonic decompression for patients with unresectable malignant obstruction).

It is an objective of the invention to provide biodegradable stents selected from the group of coronary stents, peripheral stents, tracheal stents, bile duct stents and esophagus stents.

It is an objective of the invention to provide biodegradable implants, including coronary stents containing fine-grained metallic materials comprising iron and/or zinc with improved mechanical properties manufactured by an electroplating process.

It is an objective of the invention to provide in-vivo degradable implants including screws, nails, flat plates, curved plates, fasteners, rods, pins, wire structures, suture anchors, staples and vessel support structures such as stents, comprising iron, zinc and/or magnesium which, due to their improved mechanical strength, provide at least a 10% volume or weight saving compared to their coarse-grained counterparts and provide a commensurately reduced total metal ion release upon dissolution.

It is an objective of the invention to provide biodegradable implants comprising iron and/or magnesium using the modification of the microstructure and the implant design to minimize volume/weight and to achieve the desired strength and the desired dissolution rates.

It is an objective of the invention to provide biodegradable implant composites with increased strength, improved creep behavior and which are radiopaque or fluoroscopically visible comprising polymers coated with and/or reinforced with at least partially fine-grained iron or iron-based materials.

It is an objective of the invention to coat biodegradable implants based on biocompatible and/or biodegradable polymers such as polyanhydrides, polycaprolactone, polyglycolic acid, polylactic acids and polyphosphate esters or metallic biodegradable materials such as biodegradable magnesium stents with layers containing metallic materials comprising iron, preferably in at least partially fine-grained form, with improved mechanical properties.

It is an objective of the invention to provide biodegradable implants comprising at least partially fine-grained metallic materials which totally degrade within one to 12 months or one to 24 months and up to 120 months via a cost-effective production method. As outlined at least partially fine-grained metallic materials particularly preferred comprise at least partially fine-grained iron; however, other biocompatible and biodegradable at least partially fine-grained metals/alloys including at least partially fine-grained zinc and/or at least partially fine-grained magnesium based materials can be employed as well.

It is an objective of the invention to provide biodegradable and radiopaque biodegradable stents which degrade within one to 12 months or one to 24 months and up to 120 months or 240 months.

It is an objective of the invention to provide biodegradable stents which can be used to treat coronary artery disease at the point where blood vessels branch.

It is an objective of the invention to provide biodegradable stents comprising iron by either electroforming the perforated final stents directly or electroforming stent precursor tubes which subsequently are cut into suitable stents by employing laser cutting.

It is an objective of the invention to provide biodegradable implants comprising at least partially fine-grained iron, zinc and/or magnesium of increased strength and hardness, low surface roughness, a low coefficient of friction resulting in reduced stent volumes and weights, ease of insertion, and commensurately reduced metal ion release upon dissolution than their coarse-grained counterparts of equal or similar chemical composition.

It is an objective of the invention to provide biodegradable metallic implants of reduced wall thickness, size, volume and weight due to increased strength and hardness achieved through grain refinement, reducing the total amount of metal-ions released into the body.

It is an objective of the invention to provide lightweight biodegradable implants with reduced coefficients of friction benefiting stent insertion and reducing the overall total metal ion release.

It is an objective of the invention to provide biodegradable implants with improved yield strength, ultimate tensile strength, toughness, bending and torsional stiffness as well as resilience and to provide more uniform degradation/dissolution characteristics in bodily fluids than their coarse-grained counterparts.

It is an objective of the invention to provide biodegradable implants wherein certain metallic portions contain a first average grain-size and certain other portions contain a second average grain-size different from said first average grain-size, wherein the first material with said first average gain-size dissolves faster than said second material to maintain the integrity of the overall structure for longer than with isotropic designs.

It is an objective of the invention to provide biodegradable composite structures comprising an at least partially fine-grained metal or alloy with a first dissolution rate and a biodegradable polymer with a second dissolution rate to adjust the dissolution rate of the composite part as required as the metallic component typically has a much higher dissolution rate than the polymeric part. As an example for short term high strength applications (bone fractures) it may be beneficial to apply a metallic iron layer which is radiopaque on the outside of the part (either facing the bone or facing the tissue) to provide good lubricity and strength and to delay access of bodily fluids to the polymer preventing premature degradation and creep. For long term applications (stenting) it can be beneficial to design the part with the metallic component partially or totally embedded in the biodegradable polymer to delay the onset of metal or alloy dissolution and extend the service life and delay the deterioration of the mechanical properties of the part.

It is an objective of the invention to provide biodegradable implants based on composite designs, such as metal/metal composites of varying composition and/or grain sizes or metal/polymer composites with different components exhibiting different in-vivo degradation rates to delay the onset of implant fragmentation for as long as possible and prevent intergranular corrosion, stress corrosion cracking and/or pitting, from prematurely breaking the implant, resulting in large implant fragments potentially causing health concerns. The design objective of the biodegradable implant therefore takes into account that, particularly in coarse grained metallic structures, corrosion does not proceed uniformly resulting in an "even thinning" of the part until it is totally dissolved, but typically parts corrode and dissolve not uniformly leading to part fragmentation. A layered, graded or composite structure containing at least partially fine-grained metallic materials, however, prevents premature fragmentation.

It is an objective of the invention to provide biodegradable implants coated with pharmaceutically active substance(s) and/or having pharmaceutically active substance(s) embedded therein and wherein the implant degradation rate is used to also control the release of one or more pharmaceutically active substance(s).

It is an objective of the invention to provide biodegradable implants or their components containing one or more layers with a microstructure selected from the group of uniform grain-size and graded grain-size, which are not prone to cracking, spalling or delamination and provide stiff, strong, tough, ductile, lightweight, free-standing parts and coatings of low internal stress.

It is an objective of the invention to grade the grain size by at least 10%, preferably by at least 25%, more preferably by at least 50% and even more preferably by at least 100% and up to 2,500,000% in the deposition direction.

It is an objective of the present invention to alternate layers of soft metal deposits of one dissolution rate with harder deposit layers of the same metal with another dissolution rate. The overall "bulk" mechanical properties depend, at least in part, upon the interlayer thickness and this approach optimizes the overall macroscopic physical, mechanical and chemical properties (i.e. strength, ductility, modulus of resilience, stiffness, toughness, dissolution rate) via modification of the microstructure.

It is another objective of this invention to provide a metallic deposit of similar chemistry throughout the article in which the grain size is varied continuously and/or stepwise to change the grain size within at least partially fine-grained as well as among at least partially fine-grained, coarse-grained and amorphous, as required. Changing the microstructure from crystalline to amorphous therefore, too, is within the scope of this invention. In all cases the amorphous or preferably the at least partially fine-grained microstructure with an average grain size between 2 nm and 10 micron in the deposit extends over a cross-sectional layer thickness of at least 1.5 nm, preferably 50 nm, preferably 0.1 micron, more preferably 50 microns and even more preferably 100 microns. Ultimately, the appropriate thickness range chosen depends on the total thickness of the part and the desired overall properties.

It is an objective of this invention, for at least part of the metallic microstructure cross section with a minimum thickness of 1.5 nm, to contain the at least partially fine-grained metallic materials with a grain size between 2 nm and 10 microns. Overall, the at least partially fine-grained material is contained in a single layer or in multiple layers that in total represents at least 5%, preferably 25%, more preferably 50% and even more preferably 75% of the total cross-section layer thickness, volume and/or weight of the metallic deposit, or volume and/or weight of the entire biodegradable implant. In all cases the remaining metallic material has a coarse-grained and/or amorphous microstructure.

All these objectives are obtained in one or more embodiments of the invention.

The implants herein can be made with a convenient electroplating and/or electroforming process for manufacturing bioabsorbable implants of numerous shapes and forms including tubes, flat plates, curved plates, nails, wires, meshes, including round, oval or irregularly shaped and branched tubular stents. As outlined, however, alternative manufacturing process can be used as well although processes capable of net-shape forming the implant or implant precursor are preferred.

U.S. Pat. No. 5,433,797 (1995) and US Patent Application Publication No. US2005-0205425A1 each incorporated herein by reference in its entirety, describe DC and pulse electrodeposition processes for forming coatings or free-standing deposits of nanocrystalline metals, metal alloys or metal matrix composites for the implants herein.

As described in U.S. application Ser. No. 12/003,224 filed Dec. 20, 2007, incorporated herein by reference in its entirety, a number of electrodeposition process variables can be modified to suitably grade the deposit including, but not limited to, the cathodic current density (including overall current and application of shielding), the anodic current density, electrical pulse parameters (forward pulse on time, off time, anodic pulse on time, peak forward or reverse current density, duty cycle, pulse frequency), bath temperature, agitation conditions (pump speed, flow direction, use of eductors) and inert material additions (particulates i.e. biodegradable polymers) to form metal matrix composites (MMCs).

Biodegradable implants according to the invention can be prepared by electroplating suitable metallic compositions onto permanent (becomes part of the implant), or temporary substrates. Suitable permanent substrates include a variety of biodegradable metal substrates such as magnesium-based materials and polymeric substrates. The use of other substrates is envisioned as well, e.g. in the case of implants for use to treat bone fractures, the substrate can comprise bone materials such as apatites and hydroxyapatites, including such materials having a nanocrystalline microstructure. If required, substrates can be metallized to render them sufficiently conductive for plating, e.g., using metallization preferably by a thin layer of iron, zinc or magnesium.

Suitable biodegradable polymers for use as permanent polymeric substrates or as particulate additions to form metal matrix composites are selected from the group consisting of (i) polyglycolide (PGA), (ii) copolymers such as poly-glycolide-co-trimethylene carbonate (PGA-co-TMC), poly-(D,L-lactide-co-glycolide) (PDLLA-co-PGA), and poly-(L-lactide-co-glycolide) (PLLA-co-PGA); (iii) poly-(L-lactide) (PLLA), poly-(D,L-lactide) (PDLLA), and (v) their stereocopolymers with varying ratios of the L and D,L parts; (vi) polydioxanone (PDS); (vii) trimethylene carbonate (TMC); (viii) polyorthoester (POE); (ix) poly-c-capralacton (PCL); and (x) composite materials comprising one or more of the aforementioned polymers and/or copolymers and PLLA/tricalcium phosphate or PLLA/hydroxyapatite. Suitable fillers for biodegradable polymers include metallic powders, flakes, ribbons and short or long fibers comprising iron, zinc and/or magnesium. The biodegradable metal filler content in the biodegradable filled-polymer ranges from 0% to 90% by weight or volume and provides the desired reinforcement. Preferably, metallic reinforcements have a microstructure which is at least partially fine-grained. Reinforcing polymer based implants with at least partially fine-grained iron, zinc and/or magnesium based fibers using a molding process are possible as the softening/melting temperature of polymers remains much below the temperature inducing grain-growth in at least partially fine-grained metallic materials, which is observed at about half of the melting temperature of the fine-grained metallic material, when expressed in Kelvin.

In a subsequent step, parts containing the graded and multilayered at least partially fine-grained metallic materials can be subjected to other finishing operations as required including, but not limited to, shaping, perforating, polishing and applying suitable coatings, e.g., containing pharmaceutical drugs. Optionally, pharmaceutically active materials can be incorporated into the entire biodegradable structure to facilitate drug release over the service life of the biodegradable implant.

According to this invention, patches or sections containing the at least partially fine-grained metallic materials can be formed on selected areas of articles, without the need to coat the entire article e.g. utilizing selective deposition techniques.

The following listing describes suitable property ranges for practicing the invention:

Minimum thickness of the metallic deposit [μm]: 5, 25;

Maximum thickness of the metallic deposit [mm]: 5; 25;

Minimum thickness of an at least partially fine-grained metallic sub-layer [nm]: 1.5; 25; 50

Maximum thickness of an at least partially fine-grained metallic sub-layer [μm]: 50; 250; 500; 1,000; 5,000; 25,000.

Minimum average grain size [nm]: 2; 5; amorphous

Maximum average grain size [nm]: 250; 500; 5,000; 10,000; 500,000

Minimum metallic content [%]: 5, 10, 25

Maximum metallic content [%]: 99; 100

Alloying additions (elements present in the human body and metallic elements known to be nontoxic): alkali metals, alkaline earth metals, Al, B, C, Cu, Co, Fe, H, Mo, Mn, Nb, O, P, S, Se, Si, Ta, Ti, V, Zn and Zr.

Articles according to this invention are substantially free of toxic or potentially toxic metallic elements or elements producing toxic substances when dissolving/degrading including As, Cd, Cr, Hg, Ni, Pb, and Sb.

Minimum ductility of the metallic deposit [% elongation in tension]: 0.5; 1; 2.5

Maximum ductility of the metallic deposit [% elongation in tension]: 15; 25; 75

Minimum metal matrix composite particulate fraction [% by volume or weight]: 0; 1; 5; 10, with the remainder being metallic material matrix Maximum metal matrix composite particulate fraction [% by volume or weight]: 50; 75; 85; 95, with the remainder being metallic material matrix Minimum hardness of the metallic material deposit [VHN]: 25; 100

Maximum hardness of the metallic material deposit [VHN]: 3,000

Minimum yield strength or ultimate tensile strength of the metallic matrix deposit [MPa]: 20; 80

Maximum yield strength or ultimate tensile strength of the metallic deposit [MPa]: 2,000; 3,000

Minimum modulus of resilience [MPa]: 0.025

Maximum modulus of resilience [MPa]: 25

Minimum time to total dissolution in the body [months]: 0.5, 1

Maximum time to total dissolution in the body [months]: 12, 24, 60, 120 The metallic coatings, layers or articles optionally contain biodegradable particulates in the percentages listed above. Suitable particulate additions include organic particulates of biodegradable polymers and/or metals, metal alloys, metal oxides, metal halides and/or metal compounds where the metal portion of metal alloys, oxides, halides and compounds is selected from the group consisting of alkali metals, alkaline earth metals, Al, B, C, Cu, Co, Fe, H, Mo, Mn, Nb, O, P, S, Se, Si, Ta, Ti, V, Zn and Zr.

Particulates employed include powders and fibers. Suitable compounds for particulates, e.g., for ligament, tendon and cartilage repair fixation include phosphates, metaphosphates and polyphosphates of e.g. calcium and sodium. The particulate average particle size is typically below 10 mm, and more preferably below 1 mm. The use of long fibers, spines and continuous ribbons are contemplated as well. Suitable examples therefore include biodegradable polymer screws reinforced with a metallic spine.

For selected applications the particulate additions do not have to be biodegradable, e.g., in the case for fracture fixation hydroxyapatite powders, fibers, reinforcements or even top layers, e.g., porous or fully dense coatings can be applied to the surface of the implant to enable the bone to grow into it.

In the case of organic coatings, organic composites or the use of organic particulates suitable biodegradable polymers are chosen from the same list as the ones identified above as suitable permanent substrates.

BRIEF DESCRIPTION OF THE DRAWINGS

In order to better illustrate the invention by way of examples, descriptions are provided for suitable embodiments of the method/process/apparatus according to the invention in which.

DETAILED DESCRIPTION

Figure 1A:
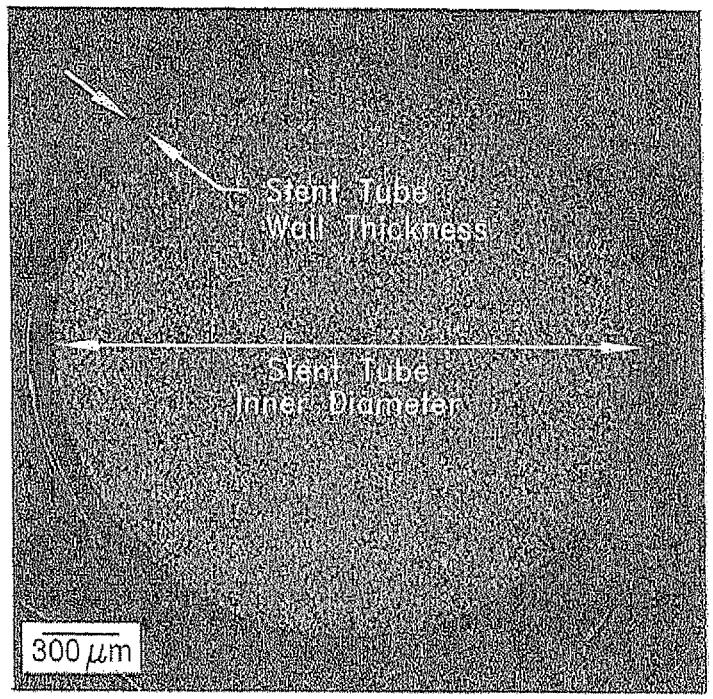
FIG. 1A is a cross-sectional view of a multilayered in-vivo biodegradable iron stent tube (ID: 2.4 mm, wall thickness: ~100 micron) according to one preferred embodiment of the invention containing alternating layers of at least partially ultra-fine-grained hard (sub layer thickness: 0.25 micron; average grain size: 30 nm) and at least partially fine-grained ductile (sub layer thickness: 1.0 micron; average grain size: 5 micron) electrolytically pure iron.

This invention discloses biodegradable articles, coatings and metallic fillers containing at least partially fine-grained metallic layers and/or coatings.

Preferred embodiments comprise iron and/or zinc produced by DC or pulse electrodeposition or other suitable synthesis methods. Metallic materials comprising iron and/or zinc can be electrodeposited from aqueous electrolytes. In one preferred embodiment the metallic material comprises "electrolytic pure iron" with an iron content of >99.5% by weight. "Unavoidable impurities" include metals such as Mn, Si, Ni, Cr, Mo and Cu and the total metallic impurities represent less than 0.4% preferably less than 0.25% of the total weight. Non metallic impurities include C, S, P, Cl and O and the total non-metallic impurities represent less than 0.4% preferably less than 0.25% of the total weight. Alternatively, the metallic material comprises zinc, magnesium, or their alloys or other metals and alloys that are in-vivo degradable in the body and are neither toxic nor produce toxic decomposition products.

The person skilled in the art of plating, in conjunction e.g. with U.S. Pat. No. 5,352,266 (1994), U.S. Pat. No. 5,433, 797 (1995), Patent Application Publication No. US 2005-

0205425 A1 and in U.S. Ser. No. 12/003,324 (2007) cited already, will know how to electroplate or electroform selected metals or alloys in at least partially fine-grained form by selecting suitable aqueous plating bath formulations and plating conditions. A process for depositing at least partially fine-grained multi-layers comprising iron is taught in U.S. Ser. No. 12/003,224 (2007) which is incorporated herein by reference in its entirety.

While magnesium cannot be electrodeposited from aqueous electrolytes, a number of organic electrolytes, fused salt electrolytes and ionic liquids can be employed. Other suitable fabrication processes include PVD, CVD, cold spraying, and severe plastic deformation.

Grain size reduction/grain refinement increases the strength of metallic materials thereby enabling a reduction in thickness and a significant overall component weight reduction. Depending on mechanical properties desired the grain size is suitably reduced to a desired level in order to achieve the desired strength, toughness and ductility. Specifically to biodegradable implants, grain-refinement enables a reduction in thickness, size and weight of the part to achieve the required mechanical properties thereby reducing the amounts of "foreign objects" introduced in the body which need to be biodegraded in-vivo and furthermore grain-refinement provides for uniform dissolution minimizing pitting. Reducing the grain size strongly enhances selected physical properties of the deposit as is illustrated in Tables 1 and 2 of pure iron and selected iron-alloys, which are commercially available. Grain-refinement generally improves the hardness, wear resistance, coefficient of friction, yield strength and resilience of the material, while the ductility and corrosion behavior are, however, compromised.

TABLE 1

Selected Properties of Pure Iron

| Chemical Composition | Avg. Grain Size [nm] | Hardness [VHN] |
|---|---|---|
| Fe: ≥99%: Wrought, cast iron annealed 1 hr at 930° C. | >200,000 | ~100 |
| Fe: ≥99%: Electrolytic pure iron, grain refined | ~5,000 37-50 ~10 | ~160 ~170-200 ~800 |

TABLE 2

Selected Properties of Metallic Materials Comprising Iron

| Chemical Composition | Avg. Grain Size [nm] | Ultimate Tensile Strength [MPa] | Yield Strength [MPa] |
|---|---|---|---|
| Fe: 98%: Conventional cast iron (~2% C) | >200,000 | 200 | 130 |
| Fe: 98%: low carbon steel (<0.3% C) | >200,000 | 400 | 350 |
| Fe: 98%: low carbon steel (<0.3% C) grain-refined | 500-1,000 200-500 | 720 840-950 | 700 800 |

Corrosion studies conducted on electrodeposited isotropic fine-grained nickel-alloys and cobalt-alloys have demonstrated that general passivation currents are higher than those reported in conventional polycrystalline materials indicative of enhanced corrosion rates. A significant improvement in the pitting potential, however, is observed in at least partially fine-grained metallic materials. This is usually associated with the localized corrosion resistance, particularly relating to intergranular corrosion and stress corrosion cracking. Similarly, at least partially fine-grained iron and iron-alloys corrode much more uniformly than their coarse-grained counterparts as is desired for biodegradable implants. The same behavior is observed in blood, artificial blood and blood substitutes, as well as physiologically saline solutions containing chlorides of alkali and earth-alkali elements, predominantly NaCl such as Ringer's, Hank's (with glucose) and Cigada's solutions. Care has to be taken when comparing corrosion rates as a function of the grain size as minute differences in the chemical composition can drastically change corrosion rates, e.g., even in the case of electrodeposited pure iron (>99.9% purity) various amounts of C, P and S which can be introduced into the deposit at a concentration in the range of 10 ppm to 1000 ppm from organic bath additives can significantly affect the corrosion behavior.

Conventional coarse-grained iron stents with a weight of 41 mg (equal to the monthly oral intake of iron) have been reported to be inserted into the native descending aorta of porcines to evaluate the safety of a corrodible iron stent with a peripheral stent design in a slotted tube design similar to a commercially available 316-L stent which served as control. Histopathological examination of heart, lung, spleen, liver, kidney and para-aortic lymphatic nodes demonstrated no signs of iron overload or iron-related organ toxicity. Adjacent to the iron stent struts, there was no evidence for local toxicity due to corrosion products and the study concluded that iron is a suitable metal for the production of a large-size degradable stent with no local or systemic toxicity.

Minimizing the thickness and weight of articles for numerous applications can be achieved by increasing the strength through grain size reduction. Depending on mechanical properties and the dissolution rate required the grain size is suitably adjusted. Incorporating a sufficient volume fraction of biodegradable particulates can also be used to further adjust the material properties. At least partially grain refined implants therefore meet the requirements of the various applications at much reduced volumes/weights as outlined in the objectives.

As noted above, particularly suited applications of the, at least partially fine-grained metallic materials prepared, e.g., by electroplating and/or electroforming disclosed herein include biocompatible and/or biodegradable implants, their components or their precursors.

As also noted above, manufacturing processes to prepare the biodegradable implant need to avoid any process involving exposing the at least partially fine-grained material to temperatures exceeding half of their melting temperature expressed in Kelvin to avoid grain-growth and to retain the fine-grained microstructure. This is also particularly important for composite structures and therefore, e.g., reinforcing magnesium based implants with at least partially fine-grained magnesium based fibers using a molding process, as proposed in the prior art, will not yield an implant with at least partially fine-grained fibers as intended, while electroplating alternating at least partially fine-grained and coarse grained layers of the material of the same or similar chemistry will.

Biodegradable and bioabsorbable implants containing at least partially fine-grained metallic layers comprising iron provide radiopaquecy and are particularly desired for stent applications. At least partially fine-grained metallic layers comprising iron can also be applied as coatings or as particulate additions to magnesium based or polymer based articles to render them sufficiently radiopaque.

As highlighted, stents are tubes designed to be inserted into a vessel or passageway in the human body to keep it open and maintain suitable fluid flow. They are used in narrowed sections of coronary and carotid arteries. Stents are also used for other vessel support structures such as the esophagus to treat a constriction, ureters to maintain the drainage of urine from the kidneys, and bile ducts. Stents are typically laser cut to the desired perforation geometry from minitube precursors. The shape of the pattern and the mechanical properties of the tube precursor dictate the expansion properties of the finished stent. In contrast to permanent stents, biodegradable stents are made of materials which are biocompatible but also biodegradable/bioabsorbable and they are designed to be totally dissolved by body fluids.

Ideal stent precursors are not limited by the design constraints of tubes and are conveniently and economically "tailor-made" to mimic the geometry of the vessels at the deployment site, e.g. by being cut from a block as taught in US Patent Application No. U.S. 2006-0292388 A1. Increasingly, stents are required which can be used to treat coronary artery disease at the point where blood vessels branch. Branches of vessels typically involve variable sizes, variable orientations and variable positions and need be stented with "custom made" stents to overcome all limitations highlighted before.

At least partially fine-grained biodegradable metallic implants have mechanical properties, other than ductility, superior to conventional polycrystalline coarse-grained implants which enable significant material reductions (typically ≥10%) to achieve the same overall mechanical properties as their coarse-grained counterparts. At least partially fine-grained biodegradable iron-based, magnesium-based and/or zinc based implants are therefore substantially smaller/thinner and lighter than prior art implants and therefore substantially reduce the overall release of metals in the body. With the reduced volume, weight and wall thickness the time to total dissolution of the fine-grained implants can also be reduced. Furthermore, at least partially fine-grained metallic implant surfaces are much harder, stronger, tougher and stiffer and have a lower coefficient of friction than their conventional coarse-grained counterparts.

Electroforming the precursor stent tubes or the final perforated stents rather than tube making, tube drawing and laser-cutting enhances the product yield and ensures that the mechanical properties need to be sufficient for the application only and not designed to also enable tube fabrication (i.e. deep drawing) therefore yielding biodegradable stents of the lowest possible weight. As highlighted above, grain size and composition can be used to design for the desired strengths and dissolution rates. "Homogenous" fine-grained implants have isotropic properties. Due to the stress inherent to some at least partially fine-grained metallic coatings produced by electrodeposition, a multilayer approach alternating between fine-grained (50 nm), hard but stressed and brittle and less-fine-grained (5 micron) or coarse grained (10 micron), softer but ductile and not stressed layers, offers an attractive approach for forming various biodegradable implants, including stent tubes, or perforated final stents. As highlighted, grading the grain size of the layer or deposit is another option.

"Biodegradable stents" also enable the employment of long stents and full-lesion coverage with stented segments extending over several inches enabling surgical revascularization. Since metals used in "permanent stents" introduce foreign objects to the body, they provoke inflammation, scarring, and thrombosis (clotting), and in-vivo biodegradable or bioabsorbable stents reduce or prevent some of these problems. In addition, "biodegradable stents" can be used to simultaneously act as optimal delivering devices for specific local therapy with drugs, genes or the like.

Figure 1B:
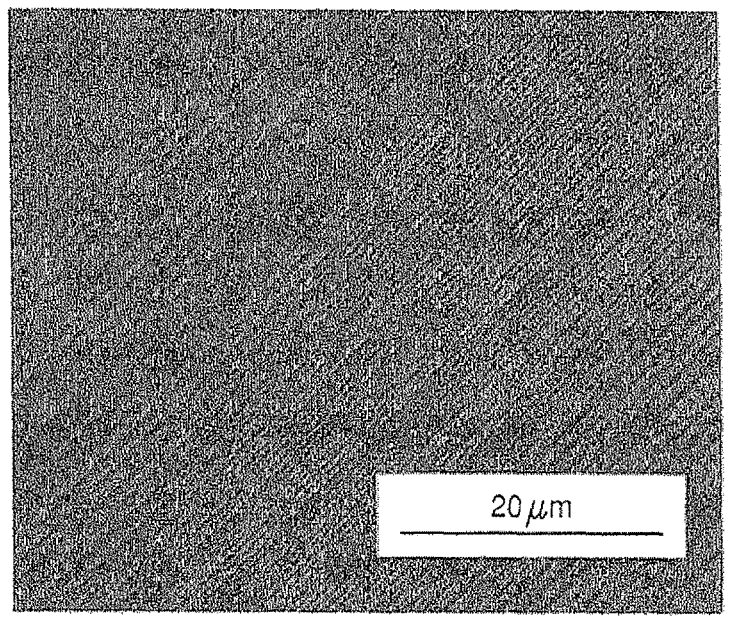
FIG. 1B is a magnified partial cross-sectional view of an etched multilayered ultra fine-grained/fine grained electrolytically pure iron stent tube.

FIG. 1A is a cross-sectional view of an electrodeposited multilayered biodegradable Fe stent tube consisting of alternating ultra fine-grained and fine-grained pure iron layers synthesized according to the process disclosed in U.S. Ser. No. 12/003,224 and available from Integran Technologies, Inc. of Toronto, Canada. A stent precursor tube (30 mm long, inner diameter: 2.4 mm, thickness: 0.10 mm) was electroformed on a temporary Ti cathode rod (still in place in the figure). The chemical composition of the stent is 99.8% Fe, 0.09% C and 0.03% S. The temporary substrate was inserted into a plating cell and rotated at 15 RPM against a stationary pure iron anode in a suitable iron chloride/iron sulfate electrolyte. Alternating ultra-fine-grained hard (sublayer thickness: 0.25 micron, average grain size 30 nm) and fine-grained ductile (sublayer thickness: 1.0 micron, average grain size 5,000 nm) layers were deposited onto the substrate by suitably modulating the electrical pulse conditions. The resulting stent has an average grain size of 40 nm in the ultra fine-grained layers and average grain size of 5,000 nm in the fine-grained layers and a wall thickness of 100 micron and is radiopaque. The layered structure is visible in FIG. 1B which is a magnified view of a partial cross-section of the etched multilayered in-vivo biodegradable iron stent tube. UTS and yield strength of the article both exceed 800 MPa and represent a mechanical strength enhancement of well over 10% when compared to the same article in coarse-grained form and the same volume/weight. After suitably perforating the stent tube to form the in vivo biodegradable stent, it is inserted into a coronary artery and suitably provides artery wall support and prevents restenosis and biodegrades after about one month and before three months. As the stent is radiopaque, the degree of degradation can be visualized and followed with time using X-rays. Similarly, multilayered or graded structures can be formed for use in other implants in free standing forms such as plates, screws, etc. Alternatively, metallic precursors can be prepared using this approach for use in composites, i.e., in the form of fibers, platelets or spines, to be incorporated into biodegradable polymeric articles, again meeting the objective of providing biodegradable implants with reduced volume/weights over implants containing only coarse-grained metallic materials.

Similarly, multilayered plates were fabricated using the same process and formed on a polished Ti cathode plate. After removal from the temporary substrate, selected plates of this material were crushed to form platelets and after sieving out and discarding the fines (through Tyler Mesh 10) the remaining particulates were added to a biodegradable polymer, specifically Poly(D,L-Lactide) available from in Sigma Aldrich Canada, Oakville, Canada) in the amount of 10% per volume and the composite compression molded into a screw for use in fracture fixation.

Figure 2:
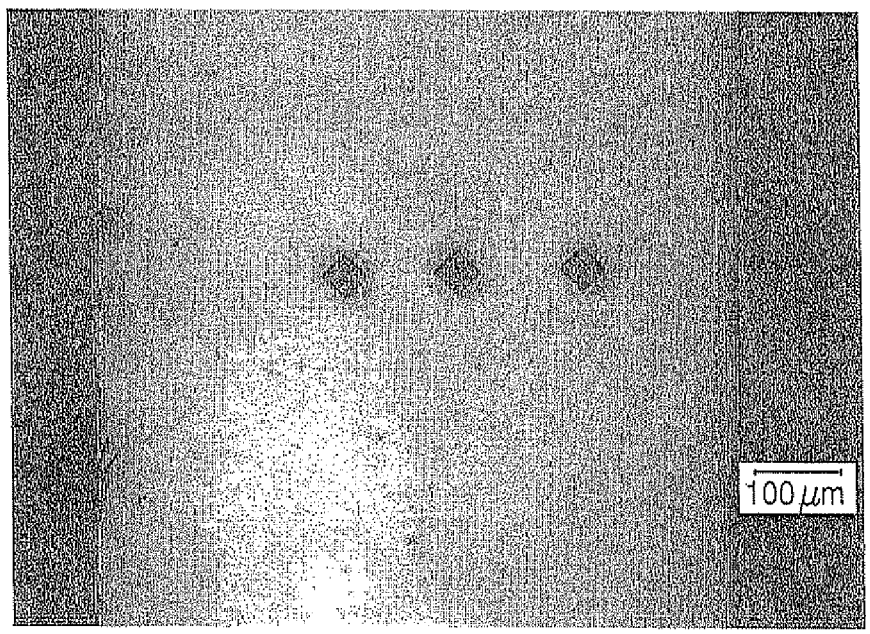
FIG. 2 is a cross-sectional view of an in-vivo biodegradable monolithic fine grained iron plate approximately 750 micron thick prepared by severe plastic deformation as used for fracture fixation according to another preferred embodiment of the invention.

Furthermore, fine-grained zinc articles or layers are also known to be produced by various processes as outlined including using pulse electrodeposition as highlighted in U.S. Pat. No. 5,352,266 (1994), U.S. Pat. No. 5,433,797 (1995), US Patent Application Publication No. US 2005-0205425 A1 and in U.S. Ser. No. 12/003,324 (2007) cited already. Specifically to fine-grained zinc a suitable electrolyte and detailed plating conditions can be found in Saber et al, "Pulse Electrodeposition of Nanocrystalline Zinc" Materials Science and Engineering A341 (2003) 174-181. Fine-grained zinc can be applied as coatings e.g. to the at least partial fine grained iron structures, magnesium and biodegradable polymer substrates noted above. 5-10 micron thick fine-grained zinc coatings were applied to several articles, including the stent tubes and the fracture fixation plates as shown in FIGS. 1A, and 2, respectively. Alternatively, at least partially fine-grained zinc articles can be electroformed.

As highlighted, using electroplating/electroforming biodegradable, at least partially fine-grained, metal plates can be shaped to mimic the desired geometry of the implant site. Furthermore plates can be conveniently grain-refined using severe plastic deformation or other processing methods, as outlined. Shaping can also be performed using suitable bending, pressing and other forming techniques.

As also highlighted above severe plastic deformation processes are suitable methods for grain refinement and creating a fine-grained microstructure in metals and alloys. Various coarse-grained metallic materials were sourced from Goodfellow Corporation of Oakdale, USA, including high purity iron foil 1 mm thick (purity 99.9%), high purity magnesium foil 1 mm thick (purity 99.9%), magnesium alloy foil 1 mm thick (97Mg-3Al-1Zn) and high purity zinc foil 1 mm thick (purity 99.95%). Selected samples were processed using severe plastic deformation by Ufa State Aviation Technical University of Ufa, Russia as described in Valiev et al, "Principles of Equal Channel Angular Pressing as a Processing Tool for Grain Refinement", Progress in Materials Science 51 (2006) 881-981, which is hereby included by reference in its entirety. The resulting processed metal samples exhibited an average grain size between 250 and 750 nm. Selected samples were cut into 1 mm wide strips and the resulting "fine-grained spines" were used as mechanical support for biodegradable polymer implants such as fracture fixation plates, anchors and screws. Other samples were shaped to match the geometry of bones at specific fracture fixation sites.

FIG. 2 is a partial cross-sectional view of such a monolithic in-vivo biodegradable pure iron plate approximately 750 micron thick with a hardness of 290 VHN and an ultimate tensile strength of 930 MPa as used for fracture fixation. The plate was synthesized by severe plastic deformation by Ufa State Aviation Technical University of Ufa, Russia, specifically using equal channel angular pressing (three rotations at 6 GPa applied pressure and room temperature to a hardness of 290 VHN and an ultimate tensile strength of 930 MPa) from high purity iron foil 1 mm thick (purity 99.9%), sourced from the Goodfellow Corporation of Oakdale, USA (grain size of ~25 micron, hardness of 120 VHN, ultimate tensile strength of 400 MPa). Three indentations made when determining the Vicker's hardness are visible on the sample. The plate is used for fracture fixation and holds a set fracture in place for at least one month until healing occurs and entirely degrades by month 10.

VARIATIONS

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A biodegradable medical implant comprising
   (a) between 0 to 95% by weight or volume of a biodegradable polymeric material;
   (b) a biodegradable metallic material comprising between 5 and 100% by weight or volume of Fe and/or at least 55% by weight of Zn, wherein between 5 and 100% by weight or volume of the biodegradable metallic material comprises at least one microstructure selected from the group consisting of an amorphous microstructure, a crystalline microstructure with an average grain size range between 2 nm and 500 nm, and a crystalline microstructure with an average grain size range between 500 nm and 1,000 nm; and
   said biodegradable medical implant having a maximum in vivo total dissolution time of 120 months.

2. The biodegradable medical implant according to claim 1, wherein said biodegradable metallic material comprises at least one alloying addition selected from the group consisting of alkali metals, alkaline earth metals, Al, B, C, Cu, Co, H, Mo, Mn, Nb, O, P, S, Se, Si, Ta, Ti, V, and Zr.

3. The biodegradable medical implant according to claim 1, wherein when said biodegradable metallic material comprises the crystalline microstructure, said crystalline microstructure comprises at least one property selected from the group consisting of a uniform grain size, a graded grain size, an anisotropic microstructure, and metallic layers of similar or dissimilar composition.

4. The biodegradable medical implant according to claim 1, wherein said biodegradable metallic material comprises the amorphous microstructure.

5. The biodegradable medical implant according to claim 4, wherein said biodegradable metallic material further comprises magnesium.

6. The biodegradable medical implant according to claim 1, wherein the metallic material constitutes 5 to 99% by volume or by weight of the implant and particulate addition constitutes from 85 to 1% by volume or by weight of the implant, wherein the particulate addition consists of a biodegradable polymer selected from the group consisting of (i) polyglycolide, (ii) copolymers selected from the group consisting of poly(glycolide-co-trimethylene carbonate), poly(D,L-lactide-co-glycolide) and poly(L-lactide-co-glycolide), (iii) poly(L-lactide), (iv) poly(D,L-lactide), (v) copolymers of poly(L-lactide) and poly(D,L-lactide), (vi) polydioxanone, (vii) trimethylene carbonate, (viii) polyorthoester, (ix) poly(c-caprolacton), and (x) composite materials comprising one or more of the aforementioned biodegradable polymers or copolymers and tricalcium phosphate and/or hydroxyapatite.

7. The biodegradable medical implant according to claim 1, wherein said biodegradable medical implant comprises at least one composite structure selected from the group consisting of a biodegradable metallic material applied to at least part of the internal or external surface of the biodegradable polymer, a biodegradable metal/polymer laminate, and a biodegradable polymer applied over part or all of the biodegradable metallic structure.

8. The biodegradable medical implant according to claim 1, wherein said biodegradable metallic material is partially or totally embedded in said biodegradable polymer to delay the deterioration of the mechanical properties of said biodegradable medical implant.

9. The biodegradable medical implant according to claim 1, wherein said biodegradable metallic material is used as reinforcement in biodegradable polymers.

10. The biodegradable medical implant according to claim 9, wherein said biodegradable metallic material comprises the reinforcement selected from the group consisting of powders, chips, flakes, spines, ribbons, layers, coatings, plates, tapes, tubes, complex shapes and fibers.

11. The biodegradable medical implant according to claim 1, wherein said biodegradable medical implant is an article selected from the group consisting of stents, screws, nails, plates, fasteners, rods, pins, wire structures, sutures, anchor clips and staples.

12. The biodegradable medical implant according to claim 11, wherein said article is a stent selected from the group consisting of coronary stents, peripheral stents, tracheal stents, bile duct stents and esophagus stents.

13. The biodegradable medical implant according to claim 1, wherein said article has a maximum in-vivo total dissolution time of 24 or 60 months.

14. A biodegradable medical implant comprising:
(a) between 0 to 95% by weight or volume of a biodegradable polymeric material;
(b) a biodegradable metallic material comprising between 5 and 100% by weight or volume of Fe and/or Zn, wherein between 5 and 100% by weight or volume of the biodegradable metallic material comprises at least one microstructure selected from the group consisting of an amorphous microstructure, a crystalline microstructure with an average grain size range between 2 nm and 500 nm, and a crystalline microstructure with an average grain size range between 500 nm and 1,000 nm; and
said biodegradable medical implant having a maximum in vivo total dissolution time of 120 months,
wherein when said biodegradable metallic material comprises the crystalline microstructure, said crystalline microstructure comprises at least one property selected from the group consisting of a uniform grain size, a graded grain size, an anisotropic microstructure, and metallic layers of similar or dissimilar composition, and
wherein when said biodegradable metallic material comprises layers of dissimilar chemical composition, the layers of dissimilar chemical composition are selected from the group consisting of zinc and iron, zinc and magnesium, and iron and magnesium.

15. A biodegradable medical implant composite comprising a biodegradable polymer and at least a partial biodegradable metallic material coating and/or a biodegradable metallic material reinforcement, wherein said biodegradable metallic material comprises between 5 and 100% by weight or volume of said biodegradable medical implant, said biodegradable metallic material is selected from the group consisting of Mg, Fe and Zn; and wherein between 5 and 100% of the weight of volume of said biodegradable metallic material comprises a microstructure selected from the group consisting of an amorphous microstructure, a crystalline microstructure with an average grain size range between 2 nm and 500 nm, and a crystalline microstructure with an average grain size range between 500 nm and 1,000 nm.

16. The biodegradable medical implant according to claim 15, wherein said biodegradable metallic material comprises a reinforcement selected from the group consisting of powders, chips, flakes, spines, ribbons, layers, coatings, plates, tapes, tubes, complex shapes and fibers.

17. The biodegradable medical implant according to claim 15, wherein said biodegradable medical implant is an article selected from the group consisting of stents, screws, nails, plates, fasteners, rods, pins, wire structures, sutures, anchor clips and staples.

18. The biodegradable medical implant according to claim 15, wherein said biodegradable metallic material comprises layers of dissimilar chemical composition.

19. The biodegradable medical implant according to claim 15, wherein said biodegradable metallic material forms a laminate.

20. The biodegradable medical implant according to claim 15, wherein said biodegradable medical implant is embedded with and/or coated with pharmaceutically active substances.

21. A biodegradable medical implant according to claim 15, wherein said biodegradable medical implant degrades entirely in vivo in a time selected from the group consisting of 24, 60, and 120 months.

22. The biodegradable medical implant according to claim 15, wherein said biodegradable polymer comprises between 5 and 95% by weight of said biodegradable medical implant.

* * * * *